(12) United States Patent
Stegmann et al.

(10) Patent No.: US 8,951,221 B2
(45) Date of Patent: Feb. 10, 2015

(54) METHOD AND DEVICE FOR THE TREATMENT OF GLAUCOMA

(75) Inventors: Robert Christopher Stegmann, Pretoria (ZA); Matthias Christian Grieshaber, Binningen (CH); Hans Rudolf Grieshaber, Schaffhausen (CH)

(73) Assignee: Grieshaber Ophthalmic Research Foundation, Schaffhausen (CH)

( * ) Notice: Subject to any disclaimer, the term of this patent is extended or adjusted under 35 U.S.C. 154(b) by 629 days.

(21) Appl. No.: 12/544,637

(22) Filed: Aug. 20, 2009

(65) Prior Publication Data
US 2011/0046536 A1 Feb. 24, 2011

(51) Int. Cl.
| | | |
|---|---|---|
| *A61M 5/00* | (2006.01) | |
| *A61F 9/007* | (2006.01) | |
| *A01B 1/00* | (2006.01) | |
| *A61B 19/00* | (2006.01) | |
| *A61F 9/00* | (2006.01) | |

(52) U.S. Cl.
CPC ..... *A61F 9/00781* (2013.01); *A61B 2019/5437* (2013.01); *A61B 2019/5441* (2013.01); *A61F 9/0017* (2013.01)
USPC .................... 604/8; 604/5.04; 604/9; 604/10; 604/19; 604/27; 604/28; 604/48; 604/93.01; 604/540; 604/541; 427/2.1; 427/2.24; 427/2.25; 600/398; 600/399

(58) Field of Classification Search
USPC ............................................ 604/5.04, 8–10
See application file for complete search history.

(56) References Cited

U.S. PATENT DOCUMENTS

| | | | |
|---|---|---|---|
| 5,486,165 A | 1/1996 | Stegmann | |
| 6,524,275 B1 * | 2/2003 | Lynch et al. | ............... 604/96.01 |
| 7,947,008 B2 * | 5/2011 | Grahn et al. | ...................... 604/9 |
| 2003/0236484 A1 | 12/2003 | Lynch et al. | |
| 2004/0127843 A1 * | 7/2004 | Tu et al. | .......................... 604/27 |
| 2004/0210181 A1 | 10/2004 | Vass et al. | |
| 2006/0155300 A1 | 7/2006 | Stamper et al. | |
| 2008/0228127 A1 * | 9/2008 | Burns et al. | ....................... 604/9 |
| 2010/0152698 A1 * | 6/2010 | Koehler | ....................... 604/500 |

FOREIGN PATENT DOCUMENTS

| | | |
|---|---|---|
| AT | 409586 B | 9/2002 |
| EP | 0898947 A2 | 3/1999 |
| EP | 1125568 A2 | 8/2001 |

(Continued)

OTHER PUBLICATIONS

International Search Report, dated Aug. 25, 2010.

*Primary Examiner* — Tatyana Zalukaeva
*Assistant Examiner* — Ilya Treyger
(74) *Attorney, Agent, or Firm* — Henry M. Feiereisen LLC; Ursula B. Day

(57) ABSTRACT

The invention relates to a method and device for the treatment of glaucoma, though insertion of an implant into the lumen of the Schlemm's canal to realize proper drainage of the aqueous humor, which implant is brought into its position in the Schlemm's canal by means of a catheter having a distal and a proximate portion and provided with a number of pores through which a gaseous or fluid medium which comes from a pressure source can emerge during insertion of the catheter carrying the implant into the Schlemm's canal, and while the catheter is being inserted into the Schlemm's canal the gaseous or fluid medium is released under pressure thereby expanding the Schlemm's canal and the implant and upon releasing the implant at its determined location, the catheter can be withdrawn from the Schlemm's canal.

24 Claims, 4 Drawing Sheets

(56) References Cited

FOREIGN PATENT DOCUMENTS

| WO | WO 00/64390 | 11/2000 |
| WO | WO 03/099175 | 12/2003 |
| WO | WO 2005/107664 A2 | 11/2005 |
| WO | WO 2007/087061 | 8/2007 |

* cited by examiner

METHOD AND DEVICE FOR THE TREATMENT OF GLAUCOMA

The present invention relates in general to a method and a device for the treatment of glaucoma, and more specifically to a method whereby a tube-shaped implant is introduced into Schlemm's canal which has been exposed through a scleral incision and the implant placed at a target location in the Schlemm's canal.

BACKGROUND OF THE INVENTION

In a healthy eye, the drainage of the circulating aqueous humor takes place in known manner, here not illustrated in detail, from the rear chamber to the front chamber and in the area of the irido-corneal angle (angulus irido-cornealis) drains via the trabecular meshwork into the lumen of the circular Schlemm's canal and from there reaches the blood stream via the episcleral vein system. In a pathological condition of the afflicted eye, and such obstructions as for example, a blocked Schlemm's canal, continuous drainage of the aqueous humor, which is generated by the epithelial layer of the ciliary body and renewed on an ongoing basis, is oftentimes no longer realized or is substantially reduced. Upon blockage of the Schlemm's canal, the eye's interior pressure can be elevated to such a level that the blood circulation of the optical nerve and its function is diminished which can lead to the eye disease known as glaucoma and can then lead to entire blindness in the afflicted eye.

PRIOR ART

A device for the treatment of glaucoma is known from the publication U.S. 2003/0236484 A1, where the device includes a tube-shaped catheter having a proximal and a distal portion with an injection unit disposed at the proximal portion and a casing disposed at the distal portion and insertable with the distal portion through a scleral cut, into the lumen of the Schlemm's canal. Through an insertion motion, which takes place in circumferential direction, pressurized medium from the injection unit is injected from the distal point of the distal end portion, whereby as a result the casing is being expanded in a balloon-like manner. This device is developed for the local stretching of the circular Schlemm's canal.

From the publications EP 0 898 947 A2 and EP 1 125 568 A2, a respective implant is known which is tube-shaped and made from flexible biocompatible material, which is inserted through a scleral incision in the Schlemm's canal of an eye, whereby the lumen of the circular Schlemm's canal is retained open in a local area of the approximately segment-shaped implant, in order to realize the natural drainage of the aqueous humor from the Schlemm's canal via the episcleral vein system.

In order to effect a circular opening of the Schlemm's canal, the so-called circumferential dilation or canaloplasty method is also known, whereby the Schlemm's canal is being circularly stretched by means of an inserted micro-catheter and either simultaneously or subsequently injected with a high molecular visco-elastic medium by means of a so-called micro-screw. Afterwards, the micro-catheter is being removed and at the same time the Schlemm's canal stretched against the anterior chamber with means suitably placed inside the lumen, such that an extension of the trabecular tissue is realized with an increased permeability and an enhanced drainage of the aqueous humor.

These techniques in the prior art have however the drawback in that they are mostly temporary in their effect. It would therefore be desirable and advantageous to provide an improved method to obviate prior art shortcomings and to provide a more permanent solution to the drainage problem.

SUMMARY OF THE INVENTION

According to one aspect of the present invention, a method is provided as well as a device for carrying out the method, whereby a permanently controlled circulation of the aqueous humor is realized as well as the natural drainage of the aqueous humor from the anterior chamber via the trabecular tissue into the Schlemm's canal and from there, via the episcleral vein system, into the blood stream.

Accordingly, the method for treatment of glaucoma includes the steps of providing an incision in the sclera and forming a scleral flap thereby exposing the Schlemm's canal for insertion of a tube-shaped implant into the exposed Schlemm's canal; sliding a tubular implant over an axial portion of a catheter; inserting the catheter with the implant into the lumen of the Schlemm's canal in a direction of a target site; expanding the Schlemm's canal and the implant by means of pressure application; releasing the implant at the target site from the catheter; and withdrawing the catheter from the lumen of the Schlemm's canal so that the implant returns to an original shape.

In another aspect of the invention, the device for carrying out the afore-stated method includes a device for treatment of glaucoma which includes a catheter having proximal and distal portions; a tubular implant placed over the distal portion of the catheter for insertion into the Schlemm's canal in a direction of a target site, wherein the distal portion has spaced-apart bores in communication with an interior space of the catheter for injecting a medium under pressure at the target site to expand Schlemm's canal and the implant and thereby allow release of the implant from the catheter and allow withdrawal of the catheter, which then returns to an original shape.

In a further aspect of the invention, the medium for applying pressure to expand the Schlemm's canal and the implant is a gaseous medium or a fluid medium.

The present invention resolves prior art problems by providing natural drainage of the aqueous humor of an eye suffering form glaucoma and to restore and permanently maintain it in the foregoing manner such that the aqueous humor drains from the anterior chamber via the trabecular tissue into the Schlemm's canal which has been expanded either circumferentially or at a predetermined target location of the implant and from there the aqueous humor drains via the episcleral vein system into the blood stream, to thereby realize a reliable natural regulation of the eye inner pressure (intraocular pressure IOP).

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
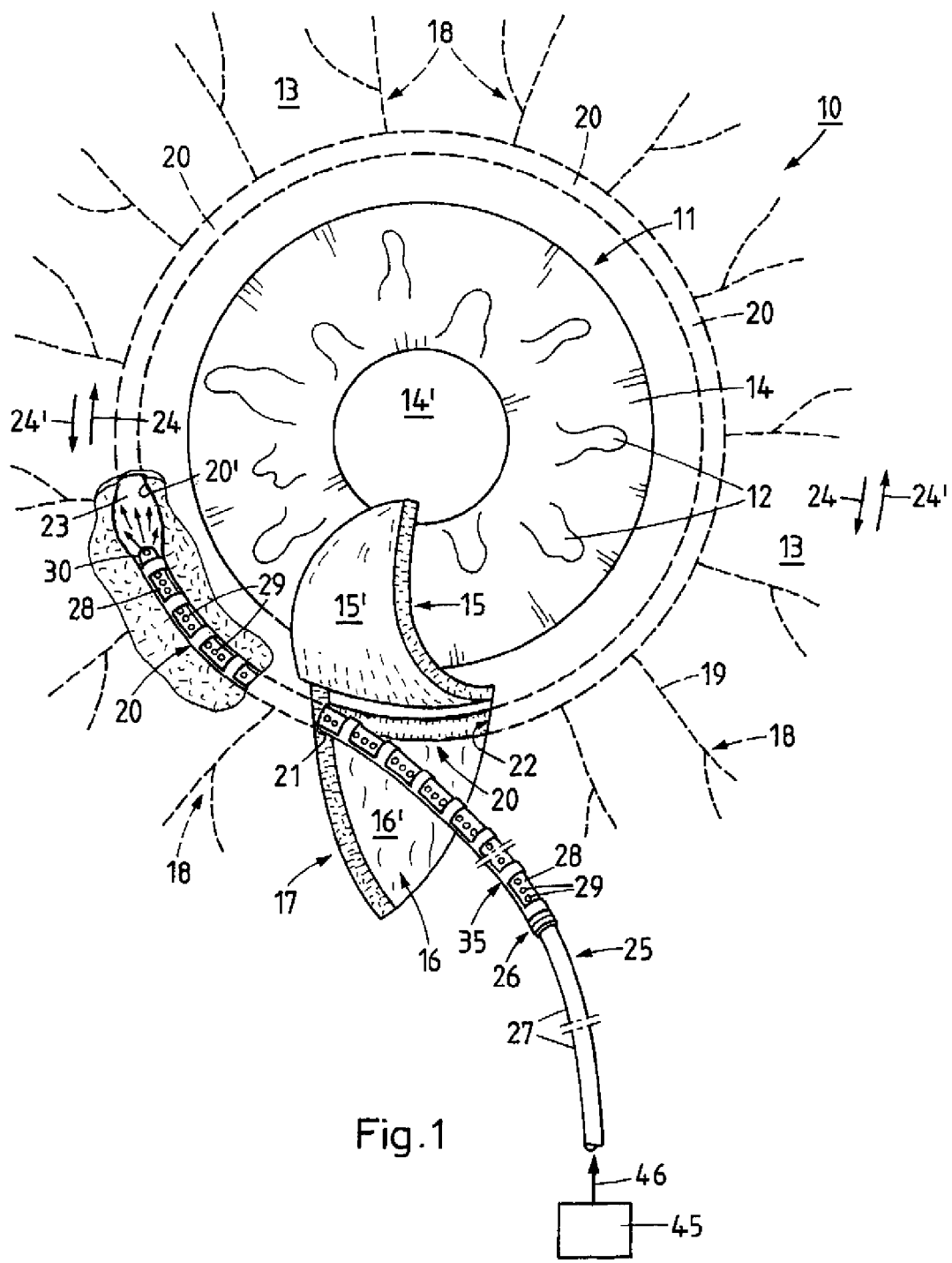
FIG. 1 is a schematic frontal view of an eye showing Schlemm's canal partially exposed by a lamellar incision for insertion of a catheter and an implant disposed at the catheter according to the present invention.

Throughout all the Figures, same or corresponding elements are generally indicated by same reference numerals.

Figure 2:
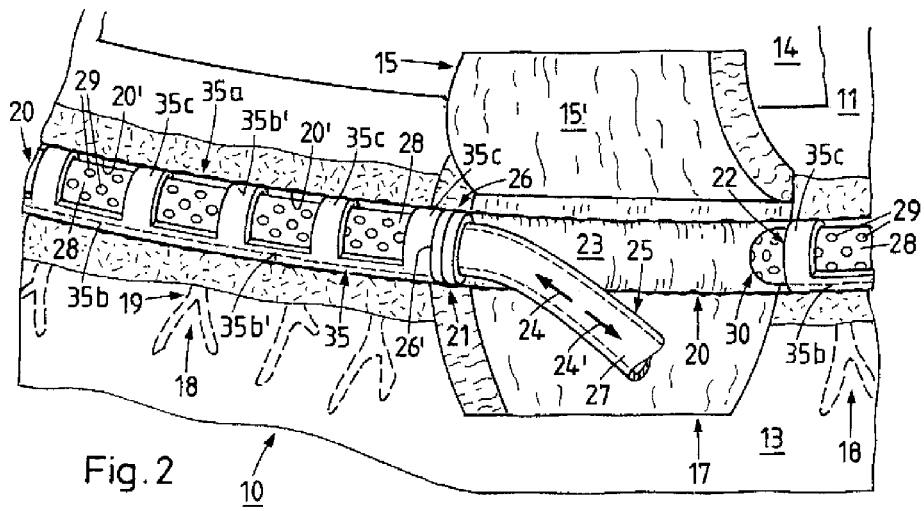
FIG. 2 is a detailed view of a portion of the eye on an enlarged scale showing the catheter with the implant disposed thereon inserted into the lumen of the Schlemm's canal.

Turning now to the drawing, and in particular for better understanding of the problems in connection with the glaucoma surgery, an eye is illustrated in FIG. 1 in a schematic front view where Schlemm's canal is seen partially exposed by an incision in the sclera for insertion of an implant disposed at the catheter. FIG. 2 shows a portion of the exposed Schlemm's canal on an enlarged scale as well as a portion of the catheter and together with the implant inserted into the lumen.

In FIG. 1 there is shown a front view of the eye 10 and the cornea 11 depicted in a schematic view, the iris 12, the sclera 13, the lens 14 with the pupil 14' as well as the circular Schlemm's canal 20 in connection with the circumferentially distributing aqueous humor channel system 18 and small canal 19. Furthermore, FIG. 1 shows the generally known partially exposed Schlemm's canal 20 (sinus venosus sclerae) through the lamellar incision 17 of a size about 3 mm by 3 mm in the sclera 13 with opened scleral flap 15. The scleral flap 15, after severing an interior scleral part which is not shown here in detail, is held in open position for further surgical procedures. The incision 17 forms a scleral bed 16 (reservoir) in the sclera 13 which is connected by oppositely located openings 21 and 22 with the Schlemm's canal 20. After insertion and local placement of the implant 35, the scleral bed 16 is being filled with a highly viscous medium (high viscosity sodium hyaluronate). When the scleral flap 15 is turned down and sewn to the sclera 13, the filled in medium prevents a connecting contact between the inner side 15' of the scleral flap 15 with the inner side 16' of the scleral bed 16.

A catheter 25 provided for the insertion and local release of the implant 35 is schematically illustrated in FIG. 1, where the implant 35 is seen slipped in axial direction over the catheter 25 (inserting instrument). For example, the catheter 25 together with the implant 35 is inserted through the first opening 21 according to arrow 24 into the lumen 23 of the circular Schlemm's canal 20. After release of the implant 35, the catheter is withdrawn according to direction of arrow 24' relative to the released implant 35 form the lumen 23 of the Schlemm's canal 20.

The catheter 25 is made of an elongated tube as illustrated in FIG. 1 and has a distal portion 28, which is provided with a head piece 30, and a proximal portion 27 adjacent the distal portion 28 in the same axial direction. The proximal portion 27 is on one end connected to a pressure source 45 by means that are not shown here in detail, in such a manner that upon insertion of the catheter 25 and upon the release of the implant 35, a biologically suitable gaseous medium or a hydrophilic fluid is being injected in direction of arrow 46 essentially through the catheter 25 into the Schlemm's canal 20.

Upon the insertion into the Schlemm's canal 20 of the distal portion 28 with the implant 35 slipped axially tightly onto it, the inner wall of the Schlemm's canal 20, with the wall of the implant 35 bearing against it becomes expanded, preferably slightly; then, due to the careful dosing of the injected medium and in the area of the distal head piece 30 Schlemm's canal becomes successively expanded in balloon-shaped manner, such that the distal portion 28 together with the implant 35 can be easily inserted into the Schlemm's canal and the implant 35 released at any chosen circumferential location, for example, at a locally afflicted site.

FIG. 2 shows on an enlarged scale a portion of eye 10 with the lamellar incision 17 and opened scleral flap 15, and for example, the distal portion 28 with the implant 35 disposed thereon, which has been inserted through a first opening 21 into the lumen 23 of the circular Schlemm's canal 20. In this embodiment, the distal portion 28, with the implant 35 has a length dimension not shown here in detail, extending form the first opening 21 along the circumference of the Schlemm's canal 20 to the oppositely located second opening 22.

As further shown in FIG. 2, the inserted distal portion 28 of the catheter 25 with the distal head piece 30 partially penetrating the second opening 22 such that the implant 35 can be released in the lumen 23 of the circular Schlemm's canal 20 and subsequently, the catheter 25, with the distal portion 28 according to arrow 24' relative to the released implant 35, can be withdrawn from the Schlemm's canal 20. For example, the so placed implant 35, upon withdrawal of the catheter form the Schlemm's canal 20 in the area of opening 22, may be held in place by means not shown here in detail, for example by pliers or forceps or similar.

At this point it is noted that the implant 35 insertable into the lumen 23 of the Schlemm's canal 20 can extend (not shown here) for example to at least a quarter, a half, three quarter or completely circumferentially form the first opening 21 up to the second opening 22. In a variant, which is not shown here, it is possible, that in a first phase, an approximately semi-circular, deformable segment of the implant 35 is inserted from the first opening 21, and in a second phase, a further, semi-circular, deformable segment of the implant 35 is inserted from the opposite, second opening 22 into the lumen 23 of the Schlemm's canal 20. By means of the inserted and released implant 35, the inner wall 20' of the Schlemm's canal 20 is being supported and the lumen 23 kept permanently open in order to realize drainage of the aqueous humor.

Furthermore, by means of the catheter 25, it is possible to insert and release an implant 35 which is curved approximately according to the radius of the Schlemm's canal 20 and is of chosen length for release at a predetermined site, for example at a locally afflicted site.

Figure 3:
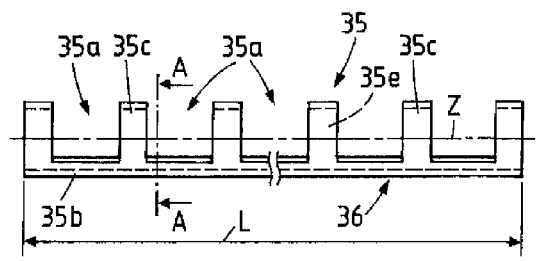
FIG. 3 is a front view on an enlarged scale of a first embodiment of the implant.

FIG. 3 shows a first embodiment of the implant 35 made from an elongated flexible tube 36. The implant 35 is of a configuration that includes a connecting part 35b continuously extending in axial direction along a longitudinal axis Z with a substantially circular-shaped cross sectional profile, and disposed thereon several ring members 35c spaced apart by recesses 35a. The circular interior space 35e of the connecting part 35b flanked by the ring members 35c, is constructed for receiving the tube-shaped distal portion 28 of the catheter 25.

The length L of the implant 35 corresponds either to the location of the afflicted site or corresponds to a distance extending from the first opening 21 to the second opening 22 of the circumference of the Schlemm's canal 20. The circular Schlemm's canal 20 has a diameter approximately from 10.0 mm to 12.0 mm which is preferably determined prior to the surgical procedure for the respective eye 10, and computed in dependence on the entire extension of the length L of the implant 35.

Figure 4:
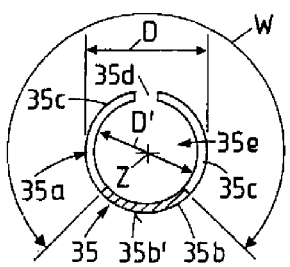
FIG. 4 is a view of the cross section of the implant according to FIG. 3 along section line A-A.

FIG. 4 illustrates the cross section of the circular ring-shaped implant 35 having an outer diameter D and an inner diameter D' according to the section line A-A as per FIG. 3, showing the connection part 35b and ring member 35c bordering the circular interior 35e. Each of the ring members 35c, located at a distance from each other at the connection part 35b, opposite the connection part 35b, is separated by a slot-shaped gap 35d. In a variant of this embodiment which is not shown here, it is also possible to configure the ring-shaped members 35c according to FIG. 3, alternatively as a non-separated ring member 35c (without the gap 35d) or with the slot-shaped gap 35d. The axially extending recesses 35a that are separating the ring members 35c respectively have an opening angle W on the order between 280° to 290°.

Figure 5:
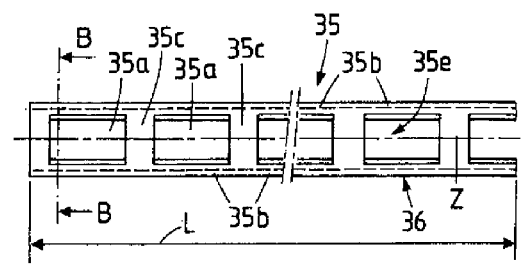
FIG. 5 is a front view on an enlarged scale of a second embodiment of the implant.

FIG. 5 shows an example of a second embodiment of an implant 35 made form a flexible elongated tube 36 and in the direction of longitudinal axis Z, two diametrically opposed connection parts 35b as well as several ring members 35c in direction of the longitudinal axis Z and distanced from each other by recesses 35a. The recesses 35a each respectively connect to the interior 35e and are configured in rectangular shape in this embodiment. However, the recesses 35a can also be of an oval, elliptical, square or trapezoidal shape. The length L of the implant 35 according to FIG. 5 is computed analog implant 35 as described in connection with FIG. 3.

Figure 6:
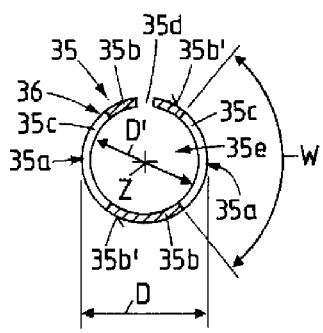
FIG. 6 is a view of the cross section of the implant of FIG. 5 along section line B-B.

FIG. 6 shows the cross section of the profile of the circular ring-shaped implant 35 according to the section line B-B in FIG. 5, where the two connecting parts 35b are shown disposed diametrically opposite relative to each other and in direction of the longitudinal axis. In one of the connecting parts 35b, the slot-shaped gap 35d oriented in direction of the longitudinal axis Z is shown in its original position and is shown by broken lines in a separated position. Furthermore, recesses 35a are shown circumferentially connected between each of the connecting parts 35b with the interior 35e of implant 35 by an opening angle W delimited between 90° and 105°. The two connecting parts that are disposed diametrically opposite each other are provided with a circular-shaped support surface 35b' relative to the longitudinal axis Z (FIG. 5).

The tube-shaped implant 35 shown in FIGS. 3 to 6 has an outer diameter D on the order of about 0.20 mm to 0.35 mm and an inner diameter D' on the order of 0.15 mm to 0.25 mm.

The maximal length L of the implant 35, which extends circumferentially, for example form the first opening 21 to the opposite second opening 22 (FIG. 1), is dependent upon the diameter of the Schlemm's canal 20, which is about 10.0 mm to 12.0 mm. The implant 35 may have a length L that is adjusted for changes in the Schlemm's canal 20 due to locally diseased sites and inserted into the lumen 23 where it is placed at the target site.

It should be noted that the implant 35 described in connection with FIGS. 3 to 6 and FIG. 11 is configured as an elongated tube made, for example, from biocompatible material, such as for example, plastic, stainless steel, special steel, as well as silver, gold platinum, nitinol or similar, preferably form biocompatible flexible material; for example, from polymeric material with thermic or mechanical shape memory effect. Implant 35 produced from flexible material with shape memory effect, especially an implant 35 that is of an approximately circular shape configured according to the Schlemm's canal 20, which at room temperature of about 18° C. to 22° C. is slipped in linear form in axial direction onto the distal portion 28 of the catheter for insertion into the Schlemm's canal 20, wherein at a body temperature of about 35° C. to 37° C., after release from the distal portion, the implant reverts to the circular form of and bearing against the lumen wall 23'. In a further variant, the implant 35 made form the elongated tube 36 is provided with a biologically active coating, for example a heparin coating.

Figure 7:
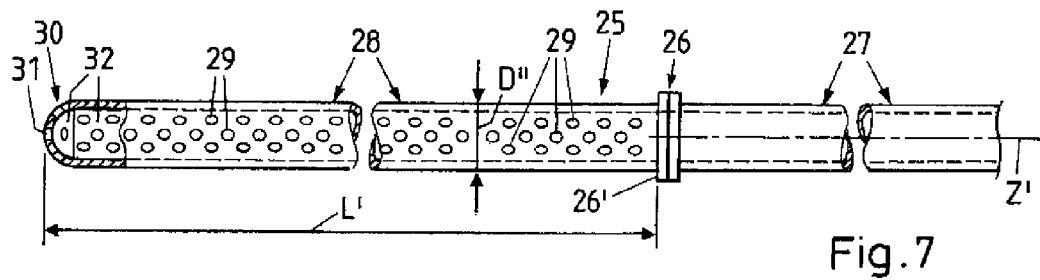
FIG. 7 is a front view of the catheter with a proximal portion and a distal portion with the head piece disposed thereon.

FIG. 7 illustrates the catheter 25 for use in the insertion of the implant 35 made from a flexible tube, respectively from a flexible mini canula and essentially includes the proximal portion 27 and the distal portion 28 disposed in the same axial direction. In a variant not shown here, the proximate portion 28 connected to the distal portion 28 is disposed laterally at the distal portion 28.

In the embodiment as shown in FIG. 7, the two tube-shaped portions 27 and 28 of the catheter having the same axial direction are removably connected to each other by means of a schematically illustrated coupling 26. The bearing edge 26' of the coupling 26 facing the distal portion 28, as schematically shown in FIG. 2, acts as a border for the implant 35 which may be axially slipped over the distal portion 28. The distal portion 28 has an outer diameter D'', which corresponds approximately to the inner diameter D' (FIG. 4, 6) of the slip-on implant 35. The circular bearing edge 26' of coupling 26 has an outer diameter equal to the outer diameter D of the implant 35.

The distal portion 28 of catheter 25, as schematically illustrated in FIG. 7, starting from the coupling 26 including the distal head piece 30 is provided with bores 29 in circumferential as well as in axial direction which connect to the interior 32 of catheter 25. The bores 29 which are essentially formed as pores acting as nozzles, for example, have a diameter of from 10 μm to 25 μm and are bored into the tube-shaped distal portion 28 by means of a known laser technology, preferably by means of an Excimer laser not shown here. Disposed at the front end of distal portion 28 and shown in a partial section view, is head piece 30 configured as a semi-circular cap. The head piece 30 is provided with at least one, but preferably several bores 31 across the surface and which act as injection nozzles and connect to the interior 32 of the catheter. The head piece 30 is preferably produced from light reflecting and biocompatible material or alternatively is coated with a light reflecting biocompatible film or similar.

Figure 8:
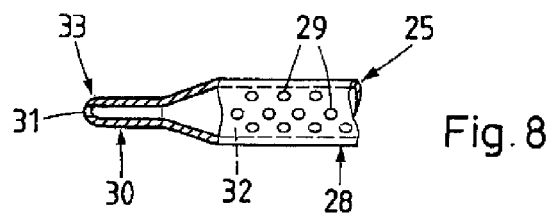
FIG. 8 is a variant of the head piece disposed at the distal end of the catheter.

FIG. 8 shows another embodiment of the head piece 30 disposed at the front end of the distal portion 28. A partial section view shows the head piece 30, starting from the outer diameter of the distal portion 28 which is provided with bores 29, tapering in direction of a front tip 33 and connected with the interior by means of bore 31 acting as a nozzle.

Figure 9:
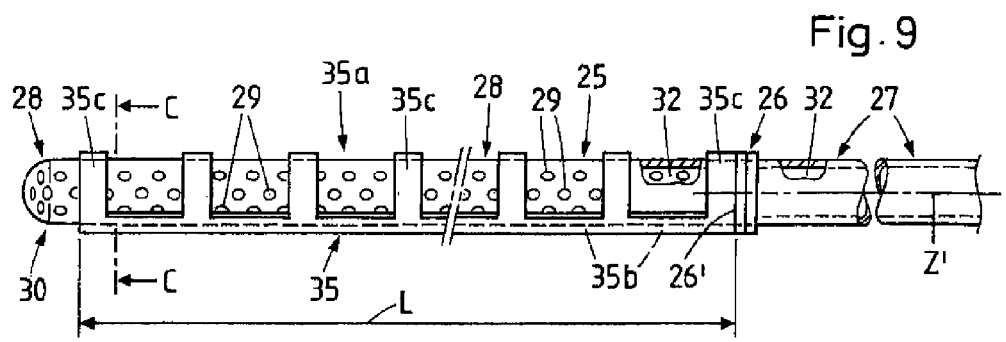
FIG. 9 is a front view of the catheter with the head piece and the implant according to FIG. 3 disposed thereon.

FIG. 9 shows a partial section of the catheter 25 with the implant disposed at the distal portion 28, and the proximate portion 27 with the coupling 26, as well as the distal portion 28 with the bores 29 across the surface that connect to the interior 32. Further are shown the ring members 35c arranged at a distance from each other and the recesses 35a provided on implant 35 according to FIG. 3. The implant has been slipped onto the distal portion 28 in axial direction where it fits tightly and bears against the bearing edge 26' of coupling 26. The bearing edge 26' of the coupling 26 permits a locally exact insertion of the implant 35 at the target location in the Schlemm's canal 20. FIG. 9 shows the distal and proximal portions 27 and 28 and partially cut-away, the interior 32.

Figure 10:
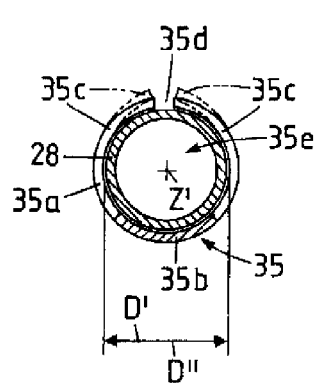
FIG. 10 is a view of the cross section of the catheter with the implant along the section line C-C as in FIG. 9.

FIG. 10 shows the catheter 25 in diameter with the slipped on implant 35 according to the section line C-C in FIG. 9, with the circular ring-shaped ring member 35c provided with the slot-shaped gap 35d, as well as the distal portion 28 of catheter 25 disposed co-axially in the interior 35e of the implant 35. The ring-shaped members 35c permit the implant 35 to be expandable upon applying pressure by a pressure medium such that the catheter 25 can be removed after the implant 35 has been placed in the target location. Upon insertion into the lumen 23 of Schlemm's canal, the semi-circular portion of the ring members 35c of the implant 35 are bearing tightly against the outer diameter D" of the distal portion 28. To achieve the release of the implant 35 at the target location, each of the ring members 35c, as schematically shown in FIG. 10, will be slightly bent outwardly at the gap as shown in broken lines relative to the interior 35e of the implant 35 in such a manner that, after placing the implant 25 at the target location, the expanded implant permits the withdrawal of the entire catheter 25 from the interior 35e according to arrow direction 24'. (FIG. 1). Once the catheter 25 has been withdrawn, the implant 35 returns to its shape before it was expanded.

For the insertion of the catheter 25 in the Schlemm's canal 20 in direction of arrow 24, a hydrophilic medium from a pressure source is being injected under a low pre-pressure such that by means of the fluid emerging from the bores 29 of the distal portion 28 and in the area of the recesses 35a of the slipped on implant 35 as well as the area at the head piece 30 of the distal portion 28, the lumen 23 of the Schlemm's canal becomes expanded in somewhat balloon-like manner (FIG. 1). As soon as the distal portion 28 with the slipped on implant 35 has been inserted circumferentially into the Schlemm's canal 20 and has reached the target location or the end position (FIG. 2), the initial pressure is increased such that the fluid emerging form the bores 29 of the inner wall of the web-shaped ring members 35c of implant 35, widens the gap 35d of the ring members 35c (FIG. 10) slightly, so that the catheter 25 with the distal portion 28 can be withdrawn form the Schlemm's canal in direction of arrow 24' (FIG. 1) relative to the released implant 35 and the ring-shaped members 35c of implant 35 return to their original shape after the catheter 25 has been withdrawn.

In another embodiment not shown here in detail, the Schlemm's canal 20 can be expanded by means of the canaloplasty method and the distal portion 28 of the Schlemm's canal with the slipped-on implant 35 inserted into the lumen 23 to the predetermined target area. Subsequently, the expansion and release of the implant 35 is effected by pressurizing the distal portion 28 connected to the proximate portion 27 through the pressure source 45, so that the fluid emerging form the bores 29 of the inner wall of the web-shaped ring members 35c of implant 35 slightly opens the gap 35d in order to effect withdrawal from the Schlemm's canal 20 in direction of arrow 24' of the catheter 25 with the distal portion 28 relative to the expanded and released implant 35.

Advantageously, the head piece 30 disposed at the front end of the distal portion 28 is coated with a reflecting material or a reflecting film or similar such that upon insertion of the distal portion 28 together with the implant 35 or withdrawal of the distal portion 28 relative to the released implant 35 into the Schlemm's canal 20, the reflecting head piece 30 is visually recognized and thus permits control of the distal portion's 28 respective position. For example, the head piece 30 is provided with a reflective fluorescence coating, whereby the reflection ceases within a millionth of a second after the light irradiation. Irradiation is carried out by means of a light source from a surgical microscope, not shown here.

Figure 11:
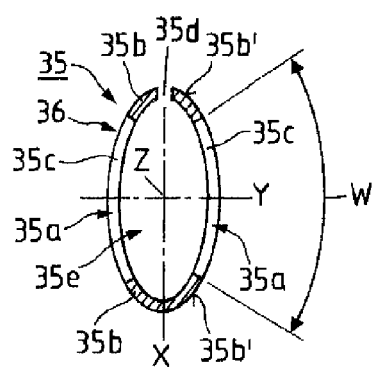
FIG. 11 shows a variant on an enlarged scale of the oval ring shaped cross section of the implant.

FIG. 11 shows a variant of the implant 35 on an enlarged scale according to section line B-B according to FIG. 5. As compared to the embodiment shown in FIG. 6, this implant 35 according to FIG. 11 has an oval-shaped diameter, preferably configured as a double symmetrical ring-shaped oval, with two axes, X and Y extending orthogonal to the longitudinal axis Z. The implant 35 configured as a double symmetrical ring-shaped oval includes two connecting parts 35b located respectively at the smaller end of the oval and oriented in direction of the longitudinal axis Z (FIG. 5). The connecting parts 35b each include a support or surface 35b', wherein one of the connecting parts 35b, at the axis Z is separated thereby forming a gap 35d. FIG. 11 also shows openings 35a with an opening angle W of between 90° and 105° at each of the longer sides of the oval which connect to the interior 35e.

Figure 12:
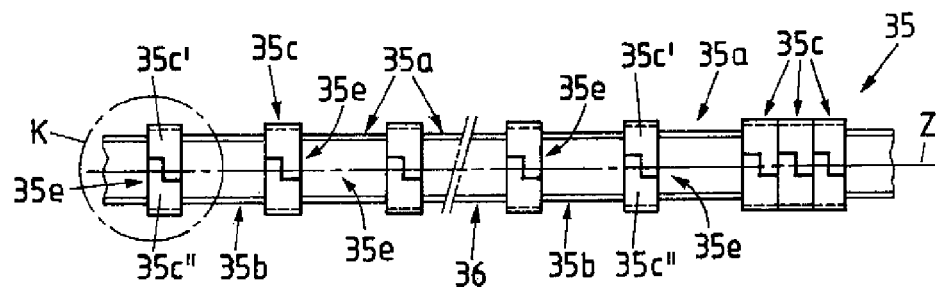
FIG. 12 is a top view of a third embodiment of the implant showing ring parts axially disposed and apart from each other at the connecting part.

FIG. 12 shows a top view of a third embodiment of the implant 35 made from the elongated flexible tube 36. The implant 35 includes the connection part 35b which extends along the longitudinal axis Z and has a substantially circular cross section, as well as the ring parts 35c that are spaced apart by the recesses 35a. The connection part 35b and the ring parts 35c having interior space 35e are constructed for receiving the tube-shaped distal portion 28 of catheter 25 (FIG. 9).

The ring parts 35c which are spaced apart by recesses 35a and disposed at tube 36 maybe also, as schematically illustrated in FIG. 12, disposed in grouped and in axial disposition of two or more ring parts 35c at any location at the implant 35.

In a variant to the first embodiment (FIG. 3) of implant 35, the ring parts 35c in the embodiment according to FIG. 12 are formed by a first ring member 35c' and a second ring member 35c" which meet at a Z-shaped gap. The approximately semi-circular shaped ring members 35c' and 35c", in their basic position according to FIG. 13, form a detachable form-fitted connection which, in accordance with FIG. 14, can be spread apart according to arrow X.

Figure 13:
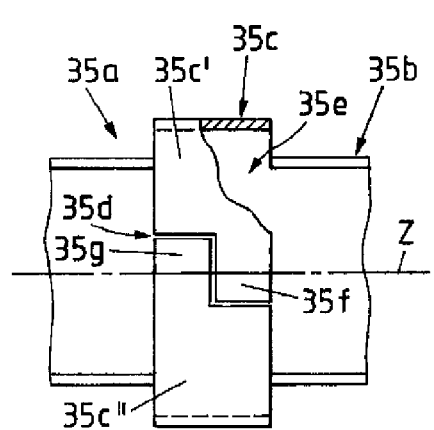
FIG. 13 shows an enlarged view designated by K of the ring part according to FIG. 12 with the gap between the two ring members in closed position.
Figure 14:
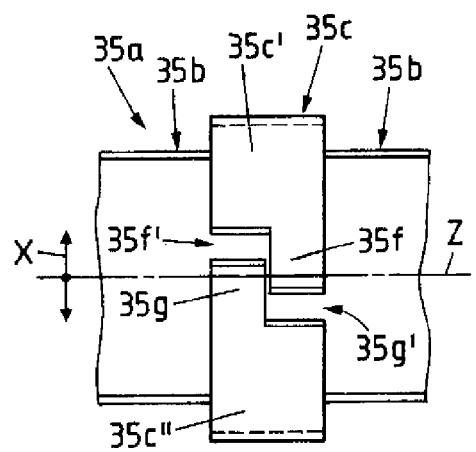
FIG. 14 shows the ring part according to FIG. 13 with the two ring members spread apart in direction of arrow X.

FIG. 13 shows an enlarged detail view of the ring part 35c as shown in FIG. 12 and designated by circle K, with the two ring members 35c' and 35c" that are separated by an approximately Z-shaped gap 35d and the axially extending connecting part 35b showing the recesses 35a. The first ring member 35c' and its interior 35e are seen in a partial section view. The ring members 35c' and 35 c" separated by the Z-shaped gap 35d, where they are facing each other, are each provided with a tongue 35f and 35g and show gaps 35f' and 35g'. In the basic position according to FIG. 13, the first tongue 35f fits into gap 35g' and tongue 35g fits into gap 35f'. When the ring members close, the two tongues 35f and 35g are sliding along each other in a relative motion perpendicular to the axis Z and in direction of arrow X along their side walls that are not shown here in detail.

Figure 15:
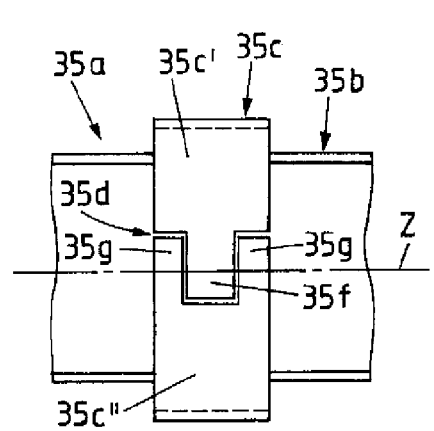
FIG. 15 shows a further variant of the ring members in closed position.
Figure 16:
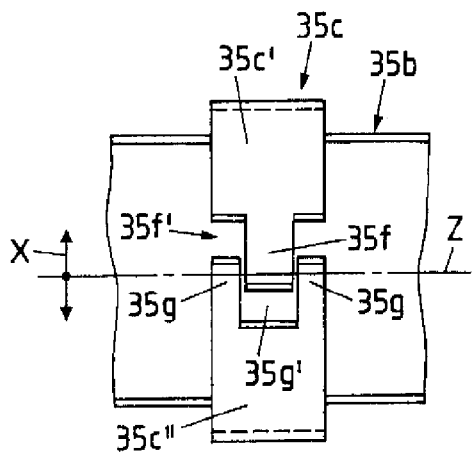
FIG. 16 the ring part of FIG. 15 with the two ring members spread apart in direction of arrow X.

FIG. 15 shows an enlarged detail view of a further embodiment of the ring part 35c with the two ring members 35c' and 35c" separated by an approximately U-shaped gap 35d and the axially extending connecting part 35b showing the recesses 35a. In this variant the first ring member 35c' is provided with a tongue 35f and the second ring member 35c" is provided with two tongues 35g with an approximately U-shaped slot 35g' in-between. In the basic position according to FIG. 16, the tongue 35f of ring member 35c' is form-fit into the U-shaped gap 35g' in a relative motion perpendicular to the axis Z and in direction of arrow X, the two tongues 35g are sliding along tongue 35f' into formfitting disposition.

While the invention has been illustrated and described as embodied in a method and device for effecting the drainage of an eye, it is not intended to be limited to the details shown since various modifications and structural changes may be made without departing in any way from the spirit of the present invention. Further practical embodiments of catheter 25, especially the portion 28 with the distal tip 30 and different configurations of the implant 35 for slipping onto the distal portion 28 are possible as well as further biocompatible materials for the respective elements, as well as for the coating and the light-reflecting foil are also possible. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A device for treatment of glaucoma, comprising:
  a catheter having proximal and distal portions;
  a flexible tubular implant configured with at least one connecting part extending along an axial extension of the implant for bearing at an inner wall at the Schlemm's canal, and radial ring members arranged in axial direction and connected to the connecting part and spaced-apart from each other by gaps, said implant placed entirely over the distal portion of the catheter for insertion into the Schlemm's canal in a direction of a target site,
  wherein the distal portion has spaced-apart bores in communication with an interior space of both, the catheter and the implant for injecting a medium under pressure at the target site to expand the implant and release the implant from the catheter at the target site to thereby allow withdrawal of the catheter, wherein the proximate portion is connected to a pressure source.

2. The device of claim 1, wherein the distal portion and the implant each have a length dimension corresponding to a circumferential length of the Schlemm's canal from a point of insertion of the distal portion into the exposed Schlemm's canal to a point where the exposed Schlemm's canal ended.

3. The device of claim 1, wherein the distal portion is removably connected to the proximate portion by means of a coupling, the coupling has a diameter corresponding to the outer diameter of the implant and includes a circular bearing surface at a side facing the implant.

4. The device of claim 1, wherein the distal portion includes a head piece configured as a cap of semi-circular shape with at least one bore in communication with the interior of the catheter.

5. The device of claim 4, wherein the head piece, beginning from the outer diameter of the distal portion is tapered into a tip having a bore in communication with the interior of the catheter.

6. The device of claim 4, wherein the head piece is made of a light-reflecting and biocompatible material.

7. The device of claim 4, wherein the head piece is coated with a light reflecting and biocompatible foil.

8. The device of claim 1, wherein the bores are distributed circumferentially and along an entire axial length of the distal portion.

9. The device of claim 8, wherein the bores are configured as pores which act as nozzles having a diameter from 10 μm to 25 μm.

10. The device of claim 9, wherein the bores are laser cut into the distal portion by an Excimer laser.

11. The device of claim 1, wherein the ring parts are divided into two ring members by an axially oriented gap, wherein the two ring members are movable relative to each other such that the gap can be increased for removal of the catheter.

12. The device of claim 11, wherein the gap is at a location on the ring part approximately opposite the connecting part.

13. The device of claim 12, wherein the two ring members are movable relative to each other upon an increase or decrease of pressure from the pressure medium.

14. The device of claim 13, wherein the gap between the ring member is approximately U-shaped or approximately Z-shaped with the ring members shaped in correspondence to the shape of the gap.

15. The device of claim 1, wherein the recesses between the ring parts have an opening angle (W) from 90° to 105°.

16. The device of claim 1, wherein the recesses between the ring parts have an opening angle (W) from 280° to 290°.

17. The device of claim 1, wherein the implant having a generally circular cross section includes two axially extending connecting parts disposed opposite from each other in circumferential direction and ring members arranged at the connection parts spaced-apart from each other by gaps, wherein one of the connecting parts is provided with a slot-shaped gap extending in axial direction and another one of the connecting parts has a surface of a shape for supporting an inner wall of the Schlemm's canal.

18. The device of claim 17, wherein the shape of the other one of the connecting parts has a circular arced surface.

19. The device of claim 17, wherein the gaps between the ring members have an opening angle from 90° to 105°.

20. The device of claim 1, wherein the implant is made of a material selected from the group consisting of biocompatible material, plastic, stainless steel, special steel, silver, gold, platinum and nitinol.

21. The device of claim 20, wherein the implant is made from polymeric material having thermal or mechanical shape memory.

22. The device of claim 20, wherein the implant is provided with a biocompatible coating.

23. The device of claim 22, wherein the coating is heparin.

24. A device for treatment of glaucoma, comprising:
  a catheter having proximal and distal portions;
    a tubular-shaped unitary implant configured with at least one connecting part extending along an axial extension of the implant for bearing at an inner wall at the Schlemm's canal, and radial ring members arranged in axial direction and connected to the connecting part and spaced-apart from each other by gaps, said implant having a plurality of openings placed in full length over the distal portion of the catheter for combined insertion into the Schlemm's canal in a direction of a target site,
  wherein the distal portion has spaced-apart bores in communication with an interior space of both, the catheter and the implant such that for injecting a medium injected under pressure at the target site for expanding can expand the implant so that the implant is released from the catheter at the target site when the catheter is withdrawn.

* * * * *